US010060469B2

(12) United States Patent
Jimenez et al.

(10) Patent No.: US 10,060,469 B2
(45) Date of Patent: Aug. 28, 2018

(54) FLEXIBLE JOINT ARRANGEMENT INCORPORATING FLEXURE MEMBERS (71) Applicant: Ex Technology, LLC, Gering, NE (US)

(72) Inventors: Omar F. Jimenez, Gering, NE (US); Nicholas R. Powley, St. Paul, MN (US)

(73) Assignee: EX TECHNOLOGY, LLC, Gering, NE (US)

( * ) Notice: Subject to any disclaimer, the term of this patent is extended or adjusted under 35 U.S.C. 154(b) by 54 days.

(21) Appl. No.: 15/198,557

(22) Filed: Jun. 30, 2016

(65) Prior Publication Data

US 2016/0377113 A1 Dec. 29, 2016

Related U.S. Application Data (63) Continuation of application No. 14/024,764, filed on Sep. 12, 2013, now Pat. No. 9,381,092, which is a (Continued)

(51) Int. Cl.
*F16C 11/12* (2006.01)
*A61F 2/44* (2006.01)
(Continued)

(52) U.S. Cl.
CPC .............. *F16C 11/12* (2013.01); *A61F 2/442* (2013.01); *A61F 2/447* (2013.01); *A61F 2/4425* (2013.01);
(Continued)

(58) Field of Classification Search
CPC combination set(s) only.
See application file for complete search history.

(56) References Cited

U.S. PATENT DOCUMENTS

| 283,218 A | 8/1883 | Rycke |
| 703,251 A | 6/1902 | Haire |

(Continued)

FOREIGN PATENT DOCUMENTS

| EP | 1342456 A1 | 9/2003 |
| EP | 1552797 A2 | 7/2005 |

(Continued)

OTHER PUBLICATIONS

PCT/US2010/042941, filed Jul. 22, 2010, International Search Report and Written Opinion, dated Apr. 25, 2011.
(Continued)

*Primary Examiner* — Daniel J Wiley
(74) *Attorney, Agent, or Firm* — Patterson Thuente Pedersen, P.A.

(57) ABSTRACT

Improved flexible joint arrangements employ at least one flexure member that interfaces with wrapping surfaces defined on the bases to which the ends of the flexure member are connected. The flexure members are configured to define a traveling instantaneous axis of rotation that moves along a path defined by the interface of the flexure and the wrapping surfaces as the bases move relative to each other. The flexure members and the bases can be constructed of a monolithic material. The wrapping surfaces of the bases can be asymmetric in cross-sectional shape. The radius of curvature of the traveling instantaneous axis of rotation can be configured to change only in discrete quantum steps without reversals. In other embodiments, the flexible joint arrangement can be configured as one or more three bar linkages in which the middle bar is rigid and the outer bars are flexure members in accordance with the various embodiments.

19 Claims, 9 Drawing Sheets

Related U.S. Application Data continuation of application No. 12/651,266, filed on Dec. 31, 2009, now Pat. No. 8,540,452.

(60) Provisional application No. 61/291,203, filed on Dec. 30, 2009, provisional application No. 61/142,104, filed on Dec. 31, 2008.

(51) Int. Cl.

| | | |
|---|---|---|
| *F16F 1/02* | (2006.01) | |
| *A61F 2/46* | (2006.01) | |
| *E05D 1/02* | (2006.01) | |
| *E05D 1/04* | (2006.01) | |
| *E05F 1/00* | (2006.01) | |
| *F16M 11/38* | (2006.01) | |
| *B33Y 80/00* | (2015.01) | |
| *A61F 2/30* | (2006.01) | |
| *A61F 2/48* | (2006.01) | |

(52) U.S. Cl.
CPC .......... *A61F 2/4455* (2013.01); *A61F 2/4611* (2013.01); *E05D 1/02* (2013.01); *E05D 1/04* (2013.01); *E05F 1/00* (2013.01); *F16F 1/025* (2013.01); *F16M 11/38* (2013.01); *A61F 2002/30485* (2013.01); *A61F 2002/30509* (2013.01); *A61F 2002/30523* (2013.01); *A61F 2002/30538* (2013.01); *A61F 2002/30556* (2013.01); *A61F 2002/30579* (2013.01); *A61F 2002/30601* (2013.01); *A61F 2002/30904* (2013.01); *A61F 2002/443* (2013.01); *A61F 2002/448* (2013.01); *A61F 2002/4475* (2013.01); *A61F 2002/482* (2013.01); *A61F 2220/0025* (2013.01); *B33Y 80/00* (2014.12); *Y10T 403/45* (2015.01); *Y10T 403/54* (2015.01)

(56) References Cited

U.S. PATENT DOCUMENTS

| | | |
|---|---|---|
| 811,344 A | 1/1906 | Wands |
| 1,388,836 A | 8/1921 | Ripsch et al. |
| 1,500,859 A | 7/1924 | Wright |
| 1,547,946 A | 7/1925 | Myers |
| 2,106,088 A | 1/1938 | De Tar |
| 2,231,221 A | 2/1941 | Rector |
| 2,453,656 A | 11/1948 | Bullard, III |
| 2,666,334 A | 1/1954 | Nalle |
| 2,711,105 A | 6/1955 | Williams |
| 2,842,976 A | 7/1958 | Young |
| 2,891,408 A | 6/1959 | Burt, Jr. |
| 3,386,128 A | 6/1968 | Vyvyan |
| 3,449,971 A | 6/1969 | Posh |
| 3,575,475 A | 4/1971 | Boerner |
| 3,596,863 A | 8/1971 | Kaspareck |
| 3,597,938 A | 8/1971 | Hellen |
| 3,700,289 A | 10/1972 | Bilinski et al. |
| 3,700,290 A | 10/1972 | Ensinger |
| 3,708,925 A | 1/1973 | Ainoura |
| 3,709,132 A | 1/1973 | Farrell et al. |
| 3,916,596 A | 11/1975 | Hawley |
| 3,985,000 A | 10/1976 | Hartz |
| 3,988,906 A | 11/1976 | Smith |
| 4,261,211 A | 4/1981 | Haberland |
| 4,396,047 A | 8/1983 | Balkus |
| 4,478,109 A | 10/1984 | Kobelt |
| 4,516,303 A | 5/1985 | Kloster |
| 4,528,864 A | 7/1985 | Craig |
| 4,559,717 A | 12/1985 | Scire et al. |
| 4,630,495 A | 12/1986 | Smith |
| 4,691,586 A | 9/1987 | van Leijenhorst et al. |
| 4,694,703 A | 9/1987 | Routson |
| 4,869,552 A | 9/1989 | Tolleson et al. |
| 5,133,108 A | 7/1992 | Esnault |
| 5,172,442 A | 12/1992 | Bartley et al. |
| 5,181,371 A | 1/1993 | Deworth |
| 5,196,857 A | 3/1993 | Chiappetta et al. |
| 5,198,932 A | 3/1993 | Takamura |
| 5,222,986 A | 6/1993 | Wright |
| 5,313,852 A | 5/1994 | Arena |
| 5,374,556 A | 12/1994 | Bennett et al. |
| 5,439,377 A | 8/1995 | Milanovich |
| 5,445,471 A | 8/1995 | Wexler et al. |
| 5,554,191 A | 9/1996 | Lahille et al. |
| 5,645,599 A | 7/1997 | Samani |
| 5,653,763 A | 8/1997 | Errico et al. |
| 5,664,457 A | 9/1997 | Nejati |
| 5,904,479 A | 5/1999 | Staples |
| 5,960,670 A | 10/1999 | Iverson et al. |
| 5,980,252 A | 11/1999 | Samchukov et al. |
| 5,988,006 A | 11/1999 | Fleytman |
| 6,039,761 A | 3/2000 | Li et al. |
| 6,045,579 A | 4/2000 | Hochshuler et al. |
| 6,056,491 A | 5/2000 | Hsu |
| 6,080,193 A | 6/2000 | Hochshuler et al. |
| 6,136,031 A * | 10/2000 | Middleton .......... A61F 2/30744 623/17.16 |
| 6,175,989 B1 | 1/2001 | Carpentar et al. |
| 6,315,797 B1 | 11/2001 | Middleton |
| 6,350,317 B1 | 2/2002 | Hao et al. |
| 6,378,172 B1 | 4/2002 | Schrage |
| 6,395,035 B2 | 5/2002 | Bresina et al. |
| 6,454,806 B1 | 9/2002 | Cohen et al. |
| 6,454,807 B1 | 9/2002 | Jackson |
| 6,484,608 B1 | 11/2002 | Ziavras |
| 6,517,772 B1 | 2/2003 | Woolf |
| 6,554,526 B1 | 4/2003 | Egelandsdal |
| 6,616,695 B1 | 9/2003 | Crozet et al. |
| 6,641,614 B1 | 11/2003 | Wagner et al. |
| 6,719,796 B2 | 4/2004 | Cohen et al. |
| 6,752,832 B2 | 6/2004 | Neumann |
| 6,772,479 B2 | 8/2004 | Hinkley et al. |
| 6,802,229 B1 | 10/2004 | Lambert |
| 6,808,537 B2 | 10/2004 | Michelson |
| 6,863,673 B2 | 3/2005 | Gerbec et al. |
| 6,932,844 B2 | 8/2005 | Ralph et al. |
| 6,953,477 B2 | 10/2005 | Berry |
| 7,018,415 B1 | 3/2006 | McKay |
| 7,051,610 B2 | 5/2006 | Stoianovici et al. |
| 7,070,598 B2 | 7/2006 | Lim et al. |
| 7,087,055 B2 | 8/2006 | Lim et al. |
| 7,201,751 B2 | 4/2007 | Zucherman et al. |
| 7,273,373 B2 | 9/2007 | Horiuchi |
| 7,308,747 B2 | 12/2007 | Smith et al. |
| 7,316,381 B2 | 1/2008 | Häcker et al. |
| 7,410,201 B1 | 8/2008 | Wilson et al. |
| 7,425,103 B2 | 9/2008 | Perez-Sanchez |
| 7,431,735 B2 | 10/2008 | Liu et al. |
| 7,435,032 B1 * | 10/2008 | Murphey ............... B64G 1/222 16/225 |
| 7,547,325 B2 | 6/2009 | Biedermann et al. |
| 7,584,682 B2 | 9/2009 | Hsiao |
| 7,611,538 B2 | 11/2009 | Belliard et al. |
| 7,632,281 B2 | 12/2009 | Errico et al. |
| 7,674,296 B2 | 3/2010 | Rhoda et al. |
| 7,682,376 B2 | 3/2010 | Trieu |
| 7,708,779 B2 | 5/2010 | Edie et al. |
| 7,712,389 B2 | 5/2010 | Wang |
| 7,753,958 B2 | 7/2010 | Gordon et al. |
| 7,758,645 B2 | 7/2010 | Studer |
| 7,758,648 B2 | 7/2010 | Castleman et al. |
| 7,892,285 B2 | 2/2011 | Viker |
| 7,896,919 B2 | 3/2011 | Belliard et al. |
| 7,901,409 B2 | 3/2011 | Canaveral et al. |
| 7,947,078 B2 | 5/2011 | Siegal |
| 7,985,256 B2 | 7/2011 | Grotz et al. |
| 8,057,549 B2 | 11/2011 | Butterman et al. |
| 8,070,813 B2 | 12/2011 | Grotz et al. |
| 8,088,163 B1 | 1/2012 | Kleiner |
| 8,192,495 B2 | 6/2012 | Simpson et al. |
| 8,303,663 B2 | 11/2012 | Jimenez et al. |
| 8,496,706 B2 | 7/2013 | Ragab et al. |

(56) References Cited

U.S. PATENT DOCUMENTS

| | | |
|---|---|---|
| 8,523,944 B2 | 9/2013 | Jimenez et al. |
| 8,540,452 B2 | 9/2013 | Jimenez et al. |
| 8,628,577 B1 | 1/2014 | Jimenez |
| 8,636,746 B2 | 1/2014 | Jimenez et al. |
| 8,771,360 B2 | 7/2014 | Jimenez et al. |
| 8,795,366 B2 | 8/2014 | Varela |
| 8,894,712 B2 | 11/2014 | Varela |
| 8,906,100 B2 | 12/2014 | Jimenez |
| 8,932,302 B2 | 1/2015 | Jimenez et al. |
| 8,940,049 B1 | 1/2015 | Jimenez et al. |
| 9,358,125 B2 | 6/2016 | Jimenez et al. |
| 9,474,626 B2 | 10/2016 | Jimenez |
| 9,486,328 B2 | 11/2016 | Jimenez |
| 9,498,270 B2 | 11/2016 | Jimenez |
| 9,668,879 B2 | 6/2017 | Jimenez et al. |
| 9,867,717 B2 | 1/2018 | Jimenez |
| 2002/0128716 A1 | 9/2002 | Cohen et al. |
| 2002/0138146 A1 | 9/2002 | Jackson |
| 2003/0077110 A1 | 4/2003 | Knowles |
| 2003/0233145 A1 | 12/2003 | Landry et al. |
| 2004/0049271 A1 | 3/2004 | Biedermann et al. |
| 2004/0111157 A1 | 6/2004 | Ralph et al. |
| 2004/0153156 A1 | 8/2004 | Cohen et al. |
| 2004/0193158 A1 | 9/2004 | Lim |
| 2004/0225364 A1 | 11/2004 | Richelsoph et al. |
| 2005/0000228 A1 | 1/2005 | De Sousa et al. |
| 2005/0033431 A1 | 2/2005 | Gordon et al. |
| 2005/0095384 A1 | 5/2005 | Wittmeyer, Jr. |
| 2005/0113921 A1 | 5/2005 | An et al. |
| 2005/0113924 A1 | 5/2005 | Buttermann |
| 2005/0175406 A1 | 8/2005 | Perez-Sanchez |
| 2005/0182416 A1 | 8/2005 | Lim et al. |
| 2005/0261769 A1 | 11/2005 | Moskowitz et al. |
| 2006/0004447 A1 | 1/2006 | Mastrorio et al. |
| 2006/0004455 A1 | 1/2006 | Leonard et al. |
| 2006/0025862 A1* | 2/2006 | Villiers .............. A61F 2/4425 623/17.14 |
| 2006/0058878 A1 | 3/2006 | Michelson |
| 2006/0129244 A1 | 6/2006 | Ensign |
| 2006/0149385 A1 | 7/2006 | McKay |
| 2006/0184171 A1 | 8/2006 | Biedermann et al. |
| 2006/0247781 A1 | 11/2006 | Francis |
| 2006/0253201 A1 | 11/2006 | McLuen |
| 2006/0293752 A1 | 12/2006 | Mounmene et al. |
| 2007/0032791 A1 | 2/2007 | Greenhalgh et al. |
| 2007/0049943 A1 | 3/2007 | Moskowitz et al. |
| 2007/0083267 A1 | 4/2007 | Miz et al. |
| 2007/0093901 A1 | 4/2007 | Grotz et al. |
| 2007/0129730 A1 | 6/2007 | Woods et al. |
| 2007/0173826 A1 | 7/2007 | Canaveral |
| 2007/0185577 A1 | 8/2007 | Malek |
| 2007/0191954 A1 | 8/2007 | Hansell et al. |
| 2007/0191958 A1* | 8/2007 | Abdou .............. A61B 17/025 623/17.16 |
| 2007/0198089 A1 | 8/2007 | Moskowitz et al. |
| 2007/0219634 A1 | 9/2007 | Greenhalgh et al. |
| 2007/0222100 A1 | 9/2007 | Husted et al. |
| 2007/0250171 A1 | 10/2007 | Bonin, Jr. |
| 2007/0255415 A1 | 11/2007 | Edie et al. |
| 2007/0282449 A1 | 12/2007 | de Villiers et al. |
| 2007/0288092 A1 | 12/2007 | Bambakidis |
| 2007/0293329 A1 | 12/2007 | Glimpel et al. |
| 2007/0293948 A1 | 12/2007 | Bagga et al. |
| 2008/0026903 A1 | 1/2008 | Flugrad et al. |
| 2008/0077246 A1 | 3/2008 | Fehling et al. |
| 2008/0091211 A1 | 4/2008 | Gately |
| 2008/0100179 A1 | 5/2008 | Ruggeri et al. |
| 2008/0103601 A1 | 5/2008 | Biro et al. |
| 2008/0114367 A1 | 5/2008 | Meyer |
| 2008/0140207 A1 | 6/2008 | Olmos |
| 2008/0147194 A1 | 6/2008 | Grotz et al. |
| 2008/0154266 A1 | 6/2008 | Protopsaltis et al. |
| 2008/0161920 A1 | 7/2008 | Melkent |
| 2008/0161931 A1 | 7/2008 | Perez-Cruet et al. |
| 2008/0168855 A1 | 7/2008 | Giefer et al. |
| 2008/0183204 A1 | 7/2008 | Greenhalgh et al. |
| 2008/0188941 A1 | 8/2008 | Grotz |
| 2008/0210039 A1 | 9/2008 | Brun |
| 2008/0221694 A1 | 9/2008 | Warnick et al. |
| 2008/0234736 A1 | 9/2008 | Trieu et al. |
| 2008/0281423 A1* | 11/2008 | Sheffer .............. A61B 17/7062 623/17.11 |
| 2008/0292392 A1 | 11/2008 | Voellmer |
| 2008/0319487 A1 | 12/2008 | Fielding et al. |
| 2009/0012564 A1 | 1/2009 | Chirico et al. |
| 2009/0076614 A1* | 3/2009 | Arramon .............. A61F 2/4425 623/17.16 |
| 2009/0099568 A1 | 4/2009 | Lowry et al. |
| 2009/0164017 A1 | 6/2009 | Sommerich et al. |
| 2009/0210061 A1 | 8/2009 | Sledge |
| 2009/0222100 A1 | 9/2009 | Cipoletti et al. |
| 2009/0234362 A1 | 9/2009 | Blain et al. |
| 2009/0259316 A1 | 10/2009 | Ginn et al. |
| 2009/0299478 A1 | 12/2009 | Carls et al. |
| 2009/0306672 A1 | 12/2009 | Reindel et al. |
| 2010/0004688 A1 | 1/2010 | Maas et al. |
| 2010/0076557 A1 | 3/2010 | Miller |
| 2010/0082109 A1 | 4/2010 | Greenhalgh et al. |
| 2010/0094305 A1 | 4/2010 | Chang et al. |
| 2010/0161062 A1 | 6/2010 | Foley et al. |
| 2010/0185291 A1 | 7/2010 | Jimenez et al. |
| 2010/0192715 A1 | 8/2010 | Vauchel et al. |
| 2010/0209184 A1 | 8/2010 | Jimenez et al. |
| 2011/0015638 A1 | 1/2011 | Pischl et al. |
| 2011/0054616 A1 | 3/2011 | Kamran et al. |
| 2011/0093075 A1 | 4/2011 | Duplessis et al. |
| 2011/0112644 A1 | 5/2011 | Zilberstein et al. |
| 2011/0138948 A1 | 6/2011 | Jimenez et al. |
| 2011/0160861 A1 | 6/2011 | Jimenez et al. |
| 2011/0172774 A1 | 7/2011 | Varela |
| 2011/0270398 A1 | 11/2011 | Grotz et al. |
| 2012/0010653 A1 | 1/2012 | Seifert et al. |
| 2012/0029636 A1 | 2/2012 | Ragab et al. |
| 2012/0116518 A1 | 5/2012 | Grotz et al. |
| 2012/0158071 A1 | 6/2012 | Jimenez et al. |
| 2012/0185049 A1 | 7/2012 | Varela |
| 2012/0226357 A1 | 9/2012 | Varela |
| 2012/0271419 A1 | 10/2012 | Marik |
| 2012/0290094 A1 | 11/2012 | Lim et al. |
| 2012/0303124 A1 | 11/2012 | McLuen et al. |
| 2012/0323329 A1 | 12/2012 | Jimenez et al. |
| 2013/0053966 A1 | 2/2013 | Jimenez et al. |
| 2013/0144388 A1 | 6/2013 | Emery et al. |
| 2013/0158664 A1 | 6/2013 | Palmatier et al. |
| 2013/0197642 A1 | 8/2013 | Ernst |
| 2013/0317615 A1 | 11/2013 | Jimenez et al. |
| 2014/0012383 A1 | 1/2014 | Triplett et al. |
| 2014/0018924 A1 | 1/2014 | McManus et al. |
| 2014/0039622 A1 | 2/2014 | Glerum et al. |
| 2014/0088714 A1 | 3/2014 | Miller et al. |
| 2014/0140757 A1 | 5/2014 | Jimenez et al. |
| 2014/0156007 A1 | 6/2014 | Pabst et al. |
| 2014/0194991 A1 | 7/2014 | Jimenez |
| 2014/0236296 A1 | 8/2014 | Wagner et al. |
| 2014/0249629 A1 | 9/2014 | Moskowitz et al. |
| 2014/0343608 A1 | 11/2014 | Whiton et al. |
| 2015/0018951 A1 | 1/2015 | Leobl |
| 2015/0088258 A1 | 3/2015 | Jimenez et al. |
| 2015/0100128 A1 | 4/2015 | Glerum et al. |
| 2015/0148908 A1 | 5/2015 | Marino et al. |
| 2015/0272743 A1 | 10/2015 | Jimenez et al. |
| 2015/0272745 A1 | 10/2015 | Jimenez et al. |
| 2015/0272746 A1 | 10/2015 | Jimenez et al. |
| 2015/0351925 A1 | 12/2015 | Emerick et al. |
| 2016/0262907 A1 | 9/2016 | Jimenez |
| 2016/0356368 A1 | 12/2016 | Jimenez et al. |

FOREIGN PATENT DOCUMENTS

| | | |
|---|---|---|
| EP | 1881209 A1 | 1/2008 |
| FR | 2372998 A1 | 12/1976 |
| JP | 05-81194 | 4/1993 |
| JP | 2004-301135 A | 10/2004 |
| JP | 2008-208932 A | 9/2008 |

(56) References Cited

FOREIGN PATENT DOCUMENTS

| WO | WO 2004/026188 A2 | 4/2004 |
|---|---|---|
| WO | WO 2004/109155 A1 | 12/2004 |
| WO | WO 2005/081330 A2 | 9/2005 |
| WO | WO 2005/096975 A2 | 10/2005 |
| WO | WO 2006/094535 A1 | 9/2006 |
| WO | WO 2006/116052 A2 | 11/2006 |
| WO | WO 2006/125329 A1 | 11/2006 |
| WO | WO 2007/002583 A2 | 1/2007 |
| WO | WO 2007/009107 A2 | 1/2007 |
| WO | WO 2007/028140 A2 | 3/2007 |
| WO | WO 2007/076377 A2 | 7/2007 |
| WO | WO 2007/111979 A2 | 10/2007 |
| WO | WO 2008/137192 A1 | 11/2008 |
| WO | WO 2009/018349 A2 | 2/2009 |
| WO | WO 2010/078468 A2 | 7/2010 |
| WO | WO 2010/078520 A2 | 7/2010 |
| WO | WO 2011/011609 A2 | 1/2011 |
| WO | WO 2011/011626 A2 | 1/2011 |
| WO | WO 2014/066890 A1 | 5/2014 |

OTHER PUBLICATIONS

PCT/US2010/042915, filed Jul. 22, 2010, Search Report and Written Opinion dated Apr. 22, 2011.
PCT/US2009/069876, filed Dec. 30, 2009, International Search Report and Written Opinion dated Sep. 27, 2010, 10 pages.
PCT/US2009/069958, filed Dec. 31, 2009, International Search Report and Written Opinion dated Nov. 29, 2010, 7 pages.
PCT/US2015/055449, filed Oct. 14, 2015, International Search Report and Written Opinion dated Dec. 11, 2015, 9 pages.
PCT/US2015/032977, filed May 28, 2015, International Search Report and Written Opinion dated Sep. 21, 2015, 10 pages.
European Application No. EP 09837185.9, European Search Report dated May 14, 2013, 7 pages.
Japanese Application No. 2012-521784, JP Office Action dated Feb. 18, 2014, 8 pages.
PCT/US2013/067070, PCT Written Opinion/Search Report dated Feb. 27, 2014, 14 pages.
PCT/US2014/052913, PCT Written Opinion/Search Report dated Dec. 22, 2014, 10 pages.
European Application No. EP 10802916.6, Examination Report dated May 12, 2016, 4 pages.
Canadian Application No. 2,768,867, Office Action dated Aug. 4, 2016, 4 pages.
Canadian Application No. 2,768,867, Office Action dated Apr. 19, 2017, 4 pages.
European Application No. EP14887838.2, Extended European Search Report, dated Oct. 25, 2017, 8 pages.
Wenzel Spine, Inc., VariLift®-L Expandable Interbody Fusion Device: A proven solution for stand-alone fusion, Product Overview, 12 pages, 2010.
Peter A. Halverson, et. al., Tension-based Multi-stable Compliant: Rolling-contact Elements, Department of Mechanical Engineering, Brigham Young University, Provo UT, USA 84602, 34 pages, 2007.
Just L. Herder, Force Directed Design of Laparoscopic Forceps, ASME Design Engineering Technical Conference, 8 pages, 1998.
Alexander H. Slocum, Fundamentals of Design, 2005.
W. Küsswetter, A Supplementary Instrumentation for Posterior Fusion of Spine in Scoliosis, Archives of Orthopedic Traumatic Surgery, 1980, 1 page.
Chou et al., Efficacy of Anterior Cervical Fusion: Comparison of Titanium Cages, polyetheretherketone (PEEK) cages and autogenous bone grafts, Journal of Clinical Neuroscience, 2008, pp. 1240-1245.

Amelie Jeanneau, et. al., A Compliant Rolling Contact Joint and its Application in a 3-DOF Planar Parallel Mechanism with Kinematic Analysis, ASME, Design Engineering Technical Conferences, 9 pages, 2004.
Hunter et al., Overview of Medical Devices, Department of Radiology, University of Arizona, Aug. 2001, pp. 89-140, vol. 30, No. 4, ISSN: 0363-0188.
Medtronic Sofamor Danek USA, Inc., *CAPSTONE* Instrument Set Technique, http://www.mtortho.com/public/capstone.pdf, © 2005, 25 pages.
Medtronic, CAPSTONE PEEK Spinal System Surgical Technique, http://www.mtortho.com/public/capstone_peek_st.pdf, © 2009, 36 pages.
Website printout from https://seelio.com/w/fgf/omnilif-the-new-standard-in-spinal-deformity-correction-and-fusion?student=lumbarjax; dated Nov. 27, 2014, 5 pages.
Printout from Video for OmniLIF Anterior Insertion Approach from Lumber Jax; https://seelio.com/w/fgf/omnilif-the-new-standard-in-spinal-deformity-correction-and-fusion?student=lumbarjax; dated Nov. 27, 2014, 7 pages.
Printout from Video for OmniLIF Features from Lumber Jax; https://seelio.com/w/fgf/omnilif-the-new-standard-in-spinal-deformity-correction-and-fusion?student=lumbarjax; dated Nov. 27, 2014, 11 pages.
Application and File History for U.S. Appl. No. 12/407,608, filed Mar. 19, 2009, now U.S. Pat. No. 8,628,577, Inventors Jimenez et al.
Application and File History for U.S. Appl. No. 12/650,994 filed Dec. 31, 2009, now U.S. Pat. No. 8,523,944, Inventors Jimenez et al.
Application and File History for U.S. Appl. No. 12/651,266, filed Dec. 31, 2009, now U.S. Pat. No. 8,540,452, Inventors Jimenez et al.
Application and File History for U.S. Appl. No. 12/841,465 filed Jul. 22, 2010, now U.S. Pat. No. 8,303,663, Inventors Jimenez et al.
Application and File History for U.S. Appl. No. 12/841,869 filed Jul. 22, 2010, Now U.S. Pat. No. 9,358,125, Inventors Jimenez et al.
Application and File History for U.S. Appl. No. 13/189,410, filed Jul. 22, 2011, now U.S. Pat. No. 8,636,746, Inventor Jimenez.
Application and File History for U.S. Appl. No. 13/661,534, filed Oct. 26, 2012, now U.S. Pat. No. 8,932,302, Inventor Jimenez.
Application and File History for U.S. Appl. No. 13/591,463, filed Aug. 22, 2012, now U.S. Pat. No. 8,771,360, Inventor Jimenez.
Application and File History for U.S. Appl. No. 13/891,356, filed May 10, 2013, now U.S. Pat. No. 8,906,100, Inventor Jimenez et al.
Application and File History for U.S. Appl. No. 14/024,764, filed Sep. 12, 2013, now U.S. Pat. No. 9,381,092, Inventor Jimenez et al.
Application and File History for U.S. Appl. No. 14/153,281, filed Jan. 13, 2014, now U.S. Pat. No. 9,867,717, Inventor Jimenez.
Application and File History for U.S. Appl. No. 14/563,660, filed Dec. 8, 2014, now U.S. Pat. No. 9,445,917, Inventor Jimenez et al.
Application and File History for U.S. Appl. No. 14/242,451, filed Apr. 1, 2014, now U.S. Pat. No. 8,940,049, Inventor Jimenez et al.
Application and File History for U.S. Appl. No. 14/318,196, filed Jun. 27, 2014, now U.S. Pat. No. 9,474,626, Inventor Jimenez et al.
Application and File History for U.S. Appl. No. 14/592,507, filed Jan. 8, 2015, now U.S. Pat. No. 9,498,270, Inventor Jimenez et al.
Application and File History for U.S. Appl. No. 14/585,544, filed Dec. 30, 2014, now U.S. Pat. No. 9,486,328, Inventor Jimenez et al.
Application and File history for U.S. Appl. No. 15/164,498, filed May 25, 2016, now U.S. Pat. No. 9,668,879, Inventors: Jimenez et al.
Application and File history for U.S. Appl. No. 15/174,454, filed Jun. 6, 2016. Inventors: Jimenez et al.
Application and File history for U.S. Appl. No. 15/332,066, filed Oct. 24, 2016. Inventors: Jimenez et al.
Application and File history for U.S. Appl. No. 15/591,214, filed May 10, 2017. Inventors: Jimenez et al.

* cited by examiner

FLEXIBLE JOINT ARRANGEMENT INCORPORATING FLEXURE MEMBERS

RELATED APPLICATION

This application is a continuation of U.S. application Ser. No. 14/024,764 filed Sep. 12, 2013, now U.S. Pat. No. 9,381,092, which in turn is a continuation of U.S. application Ser. No. 12/651,266 filed Dec. 31, 2009, now U.S. Pat. No. 8,540,452, which claims the benefit of U.S. Provisional Application No. 61/291,203 filed Dec. 30, 2009, and U.S. Provisional Application No. 61/142,104, filed Dec. 31, 2008, each of which is hereby fully incorporated herein by reference.

FIELD OF THE INVENTION

The present invention relates to joint or linkage arrangements. More particularly, the present invention relates to a flexible joint arrangement including at least one flexure member that interfaces with wrapping surfaces defined on the bases to which the ends of the flexure member are connected.

BACKGROUND OF THE INVENTION

Many devices use joint arrangements to move one part of a device relative to another part of the device, such as moving between a collapsed configuration and an expanded configuration, rotating from one position to another, or performing more complicated manipulations. Joint arrangements can be designed to repeatedly move among configurations or positions, either for an infinite number of cycles or a finite number of cycles, or can be designed to move between configurations or positions only once or a limited number of times.

One approach for joint arrangements is to construct joints utilizing multiple parts where one part rotates relative to the other by means of sliding contact between components of the joint, such as a ball and socket or a pin and clevis. There are many known problems with such joints. Structures utilizing a plurality of multi-part joints can also suffer from a problem known as "dead band," in which movement at one end of the structure is not communicated to the other end until the intervening clearances in the multi-part joints are taken up. Such joints can also be difficult and expensive to manufacture to the required tolerances.

In view of these problems with rigid multi-part joints, joint arrangements comprised of straps, bands or leaf springs of flexible materials have been used, such as described in U.S. Pat. Nos. 3,386,128, 4,869,552, 5,133,108, 5,196,857 and 6,378,172. U.S. Pat. Nos. 6,175,989 and 6,772,479 describe flexible joint arrangements that utilize shape memory alloy materials. A resilient joint is disclosed in U.S. Pat. No. 7,435,032 that limits the maximum strain on the joint by connecting the ends of a flexure to cavities that limit the bend radius of the flexure to ensure that the maximum strain is not exceeded. The flexure member connects two separate structures and functions essentially like a standard leaf spring that stores the energy used to move it to the collapsed configuration in order to return to the expanded configuration.

One of the significant drawbacks of conventional designs for flexible joint arrangements is that such joints generally cannot support any significant loading in either compression or tension, and are therefore unsuitable for devices that must support such loads.

SUMMARY OF THE INVENTION

Flexible joint arrangements in accordance with various embodiments of the present invention employ at least one flexure member that interfaces with wrapping surfaces defined on the bases to which the ends of the flexure member are connected. The flexure members are configured to define a traveling instantaneous axis of rotation that moves along a path defined by the interface of the flexure and the wrapping surfaces as the bases are moved relative to each other. In one embodiment, the flexure members and the bases are constructed of a monolithic material. In another embodiment, the wrapping surfaces of the bases are asymmetric in cross-sectional shape. In other embodiments, the radius of curvature of the traveling instantaneous axis of rotation is configured to change only in discrete quantum steps without reversals. In still other embodiments, the flexible joint arrangement can be configured as one or more three bar linkages in which the middle bar is relatively rigid and the outer bars are flexure members in accordance with the various embodiments.

In an embodiment, a flexible joint arrangement includes a base, a structural member, and a flexure member connecting the structural member to the base that can comprise a one-piece unitary monolithic body. The flexure member can rotate to allow movement of the structural member relative to the base between a compressed configuration and an expanded configuration. The base and/or the structural member can define a surface referred to as a wrapping surface that provides a guide for rotation and/or wrapping of the flexure member as the structural member is moved relative to the base from the compressed configuration to the expanded configuration. In various embodiments, the wrapping surface can be concave, convex, or flat.

In another embodiment, a flexible joint arrangement includes a top base and a bottom base. A structural member is disposed intermediate the top base and bottom base and a flexure member connects each end of the structural member to the bases. The flexure members are configured to rotate to expand the structural member to allow the top base and the bottom base to move between a collapsed configuration and an expanded configuration relative to each other. The flexure members can each define a traveling instantaneous axis of rotation that moves along the interface of the flexure member and the wrapping surfaces as the top base and bottom base are moved between the collapsed configuration and the expanded configuration such that the axes of rotation travel at different heights within a plane transverse to the axes of rotation.

The thickness of the flexure in relation to the bend radius of the wrapping surface determines the fatigue life of the flexure due to movement. In some embodiments, flexures can be configured and designed to have very long fatigue life. In other embodiments, flexures can be configured and designed to have a finite fatigue life associated with a predetermined range of maximum number of cycles of expansion and contraction.

The above summary of various embodiments of the invention is not intended to describe each illustrated embodiment or every implementation of the invention. This summary represents a simplified overview of certain aspects of the invention to facilitate a basic understanding of the invention and is not intended to identify key or critical elements of the invention or delineate the scope of the invention.

BRIEF DESCRIPTION OF THE DRAWINGS

The invention may be more completely understood in consideration of the following detailed description of various embodiments of the invention in connection with the accompanying drawings, in which.

While the invention is amenable to various modifications and alternative forms, specifics thereof have been shown by way of example in the drawings and will be described in detail. It should be understood, however, that the intention is not to limit the invention to the particular embodiments described. On the contrary, the intention is to cover all modifications, equivalents, and alternatives falling within the spirit and scope of the invention.

DETAILED DESCRIPTION OF THE DRAWINGS

In the following detailed description of the present invention, numerous specific details are set forth in order to provide a thorough understanding of the present invention. However, one skilled in the art will recognize that the present invention may be practiced without these specific details. In other instances, well-known methods, procedures, and components have not been described in detail so as to not unnecessarily obscure aspects of the various embodiments of the present invention.

Figure 1:
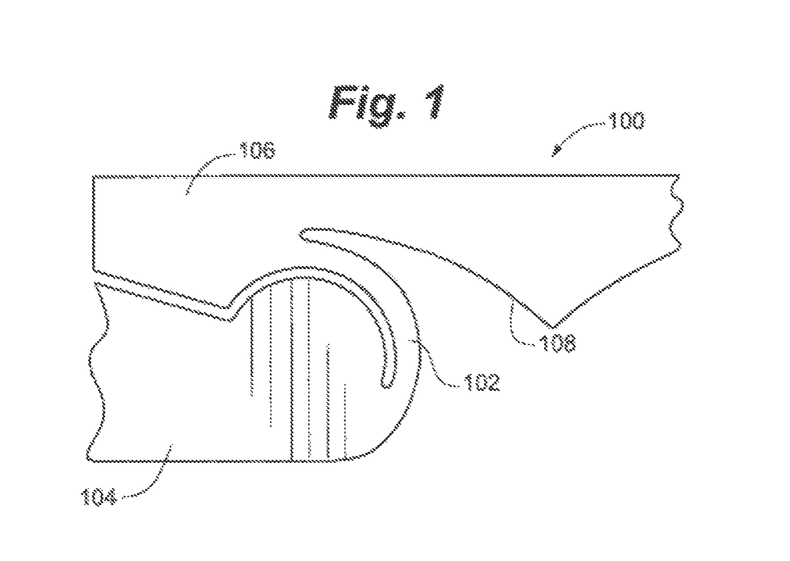
FIG. 1 is a partial side view of a flexible joint arrangement according to an embodiment of the present invention.
Figure 9:
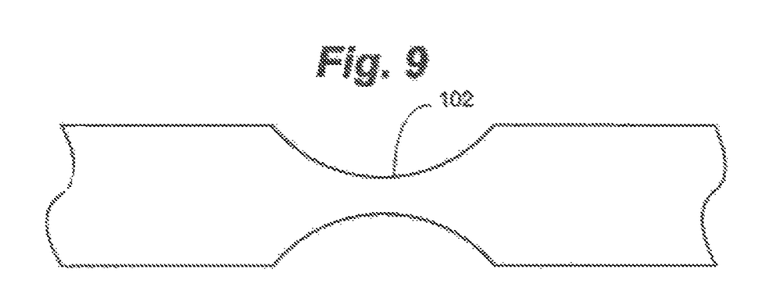
FIG. 9 is a side view of a circular flexure.
Figure 10:
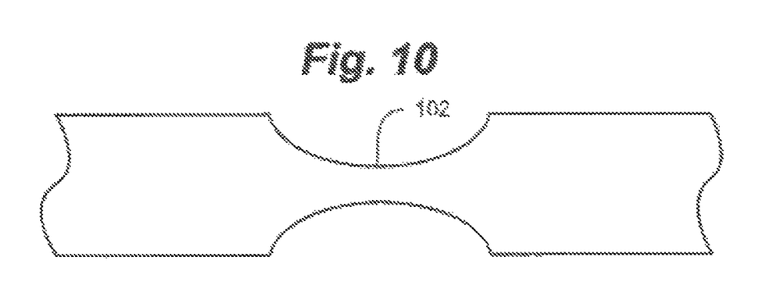
FIG. 10 is a side view of an elliptical flexure.
Figure 11:
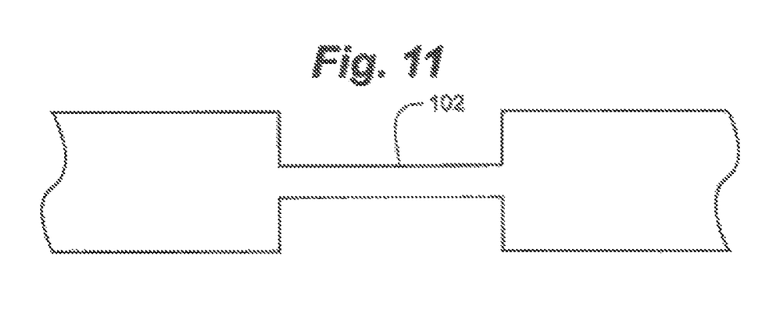
FIG. 11 is a side view of a leaf flexure.

Referring to FIG. 1, there can be seen a flexure joint or linkage 100 according to an embodiment of the present invention. Flexure linkage 100 includes a flexure member 102 connecting a structural member 104 to a base 106. A flexure member 102 is a thin, generally planar strip of material that allows movement of the structural member 104 relative to the base 106 and can support loading on the linkage 100. Structural member 104, base 106, and flexure member 102 can comprise a one piece unitary monolithic body. Flexure member 102 allows a one piece linkage 100 to behave similarly to a device having multiple parts and a rotating pin joint. Flexure members 102 can, for example, be band flexures (FIGS. 1, 2A-2C, 3A-3C and 4A-4C), circular flexures 10 (FIG. 9), elliptical flexures (FIG. 10), or leaf flexures (FIG. 11). Additionally, such flexures 102 can taper along their length or can have a curved cross-section.

Base 104 can provide a wrapping surface 108 that guides the rotation of flexure member 102 as the structural member 104 and base 106 are moved relative to each other and can provide support to flexure member 102 under loading conditions. A wrapping surface 108 can be defined as a surface that sets the radius of curvature of the flexure throughout a discrete portion of the rotation of the flexure. In the depicted embodiment, the wrapping surface 108 is shown as concave, or inwardly curved.

Figure 2A:
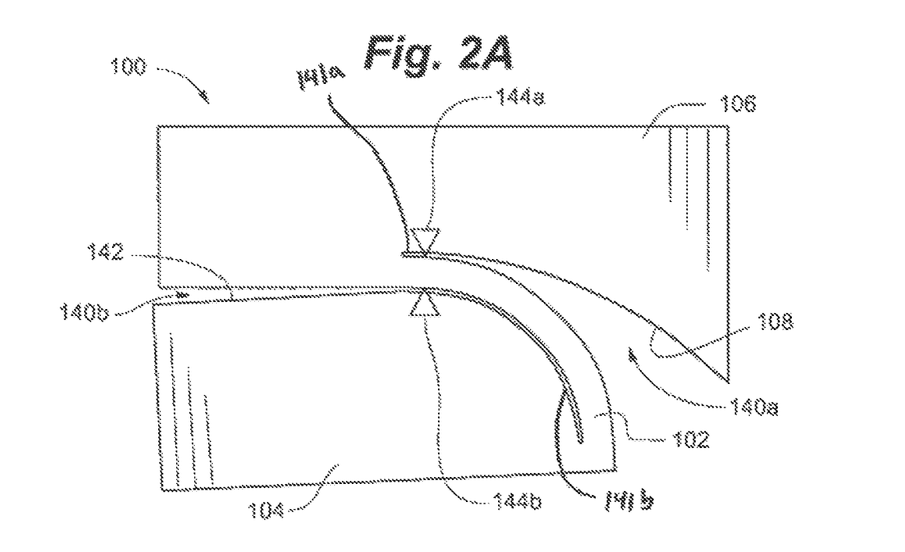
FIG. 2A is a partial side view of a flexible joint arrangement according to an embodiment of the present invention.
Figure 2B:
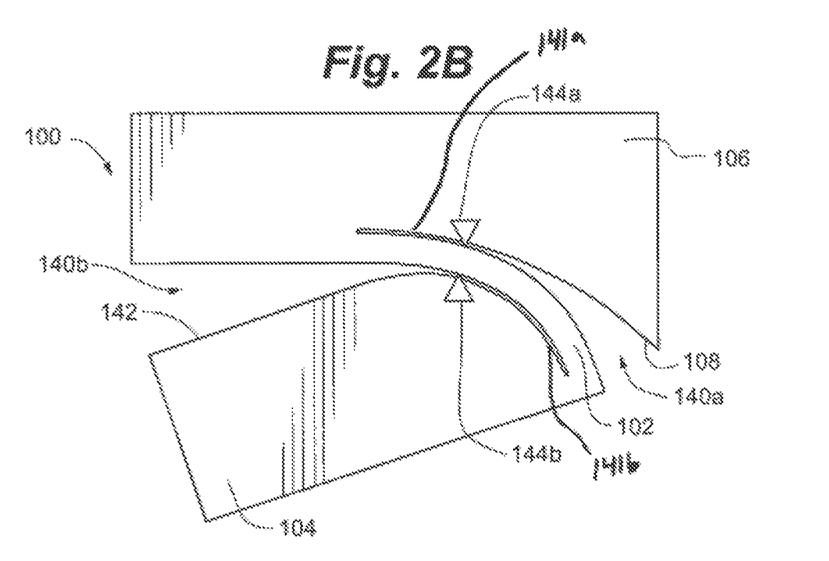
FIG. 2B is a partial side view of the flexible joint arrangement of FIG. 2A.
Figure 2C:
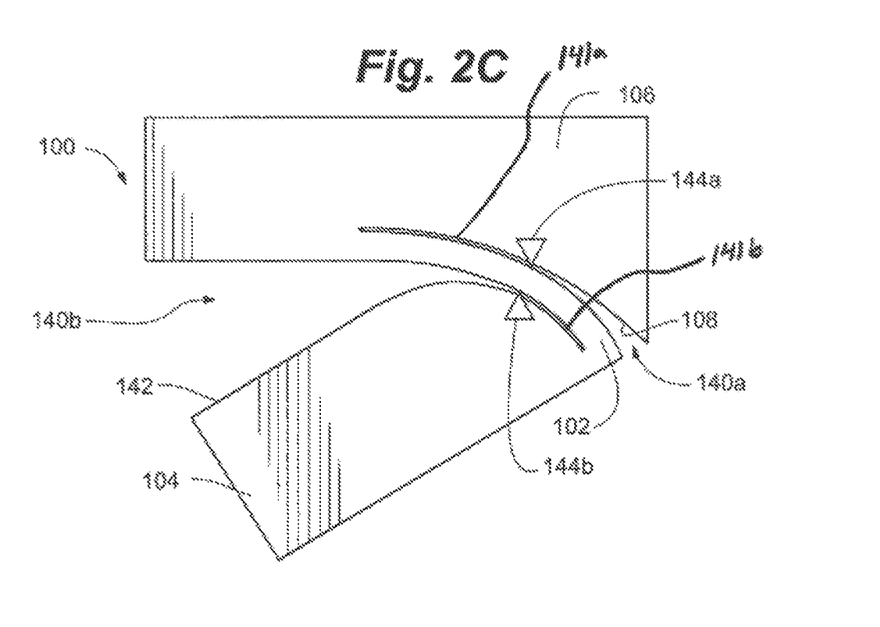
FIG. 2C is a partial side view of the flexible joint arrangement of FIG. 2A.

FIGS. 2A-2C depict the behavior of flexure member 102 as the structural member 104 is expanded relative to the base 106. Flexure member 102 defines a first open area, or kerf 140a, between wrapping surface 108 and flexure member 102 and a second kerf 140b between inner perimeter 142 of structural member 104 and flexure member 102. When the structural member 104 is in a collapsed configuration relative to base 106, kerf 140a is wider than kerf 140b. As the structural member 104 is expanded from base 106, flexure member 102 flattens out as guided by wrapping surface 108, so kerf 140b widens as kerf 140a narrows. The fulcrum around which flexure member 102 bends is shown by arrows 144a and 144b. The fulcrum 144a, 144b translates along the flexure member 102 as it bends. Fulcrum 144a, 144b therefore travels in both vertical and horizontal directions. This provides for increased expansion of the structural member 104 relative to the base 106. As the fulcrum 144a, 144b moves along the flexure member 102, a greater portion of any compressive load on the linkage 100 is supported by the structural member 104 and, accordingly, the tensile forces on the flexure member 102 are reduced. The linkage 100 of this embodiment is therefore strongest when the structural member 104 is expanded to its fullest extent relative to the base 104 such that the load is normal to the wrapping surface.

As can be seen in FIGS. 2A-2C, the inner perimeter 142 of structural member 104 also acts as a wrapping surface for the flexure 102 (and the structural member 104 could be considered a second base). The wrapping surface of the inner perimeter 142 and the wrapping surface 108 are asymmetrical to each other. Having two asymmetrical wrapping surfaces provides a joint that is better in compression and optimizes load carrying capability. As the flexure 102 rotates, the radius of curvature at any given point on the flexure 102 is defined by either the inner perimeter wrapping surface 142 or the wrapping surface 108. To the left of the fulcrum 144a, 144b, the radius of curvature is defined by the wrapping surface 108. To the right of the fulcrum 144a, 144b, the radius of curvature is defined by the inner perimeter 142. Thus, throughout its rotation each point on the flexure 102 can have only two or a limited number of discrete different radii of curvature, i.e., discrete quantum steps of radii of curvature. This is in contrast to the flexure joints described in U.S. Pat. No. 7,435,032, for example, where the flexure member acts like a leaf spring and has a continually changing radius of curvature through a predetermined range as the joint is rotated. In addition, the two radiuses of curvature that the flexure 102 can undergo are a matter of degree; they do not transition between a positive curvature and a negative curvature so as to undergo a reversal of radius of curvature, which thereby reduces the strain on the flexure.

Figure 3A:
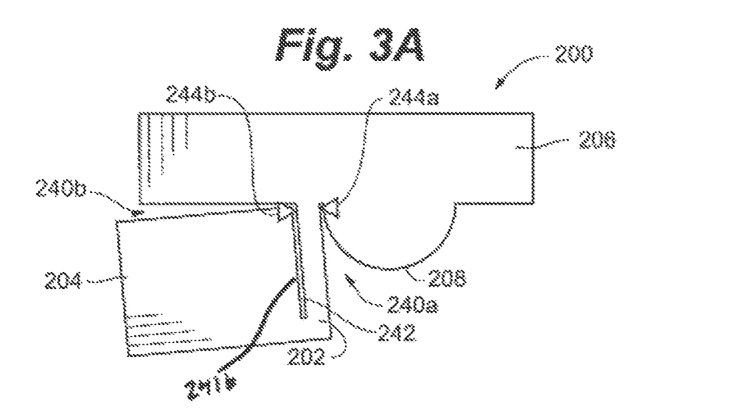
FIG. 3A is a partial side view of a flexible joint arrangement according to an embodiment of the present invention.
Figure 3B:
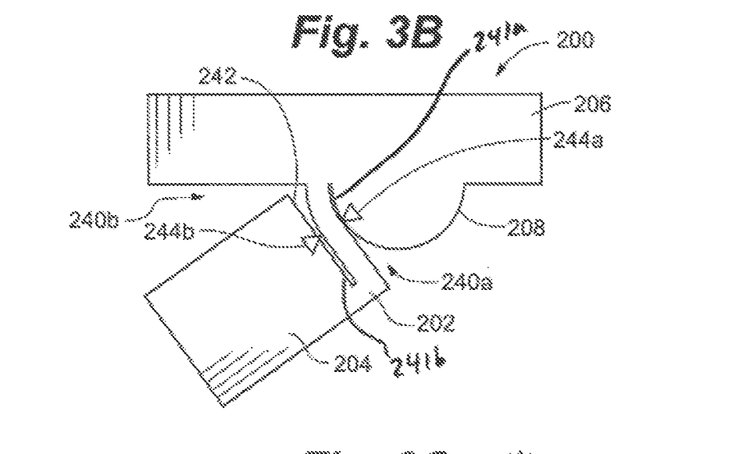
FIG. 3B is a partial side view of the flexible joint arrangement of FIG. 3A.
Figure 3C:
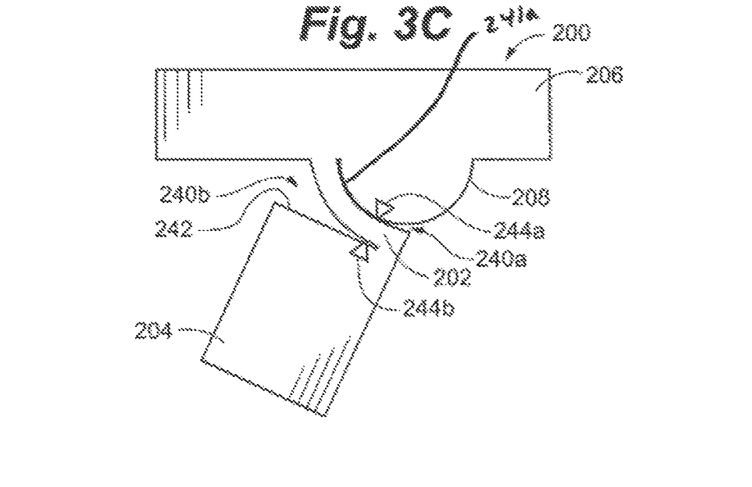
FIG. 3C is a partial side view of the flexible joint arrangement of FIG. 3A.

In an embodiment of a flexure linkage 200 shown in FIGS. 3A-3B, base 204 provides a wrapping surface 208 for flexure members 202 that is outwardly curved (in contrast to the inwardly curved wrapping surfaces 108 depicted in FIGS. 1 and 2A-2C). Flexure 202 curves around wrapping surface 208 as structural member 204 is expanded relative to base 206. In the collapsed state shown in FIG. 3A, flexure member 202 is parallel to an inner surface wrapping surface 242 of structural member 204. As the structural member 204 is expanded relative to base 206, flexure member 202 bends around wrapping surface 208, widening kerf 240b and narrowing kerf 240a. As shown by arrows 244a, 244b, the fulcrum translates along the length of flexure member 202 (in both the horizontal and vertical directions) as the device distracts. Fulcrum 244a, 244b is always perpendicular to inner surface 242 of structural member 204. This results in the entirety of a load on the linkage 200 being carried in compression by the structural member 204. Therefore, there is no tensile force on flexure member 202. This allows flexure member 202 to be easily sized to enjoy an essentially infinite fatigue life. This embodiment allows a linkage to be constructed from a material, such as nitinol, that provides strong compressive support when it is of large dimensions but that distorts easily when slender members of the same material are under tension or bending. Similar to flexure member 102, points along the flexure member 202 to the left of the fulcrum 244a, 244b have a radius of curvature defined by wrapping surface 208 and points to the right of fulcrum 244a, 244b have a radius of curvature defined by the inner perimeter wrapping surface 242 as the flexure member 202 rotates.

Figure 4A:
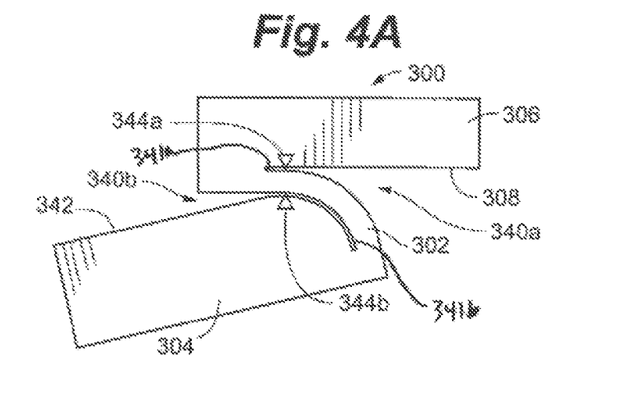
FIG. 4A is a partial side view of a flexible joint arrangement according to an embodiment of the present invention.
Figure 4B:
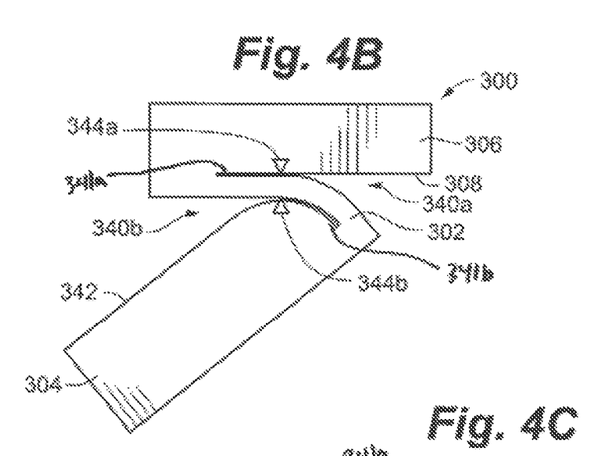
FIG. 4B is a partial side view of the flexible joint arrangement of FIG. 4A.
Figure 4C:
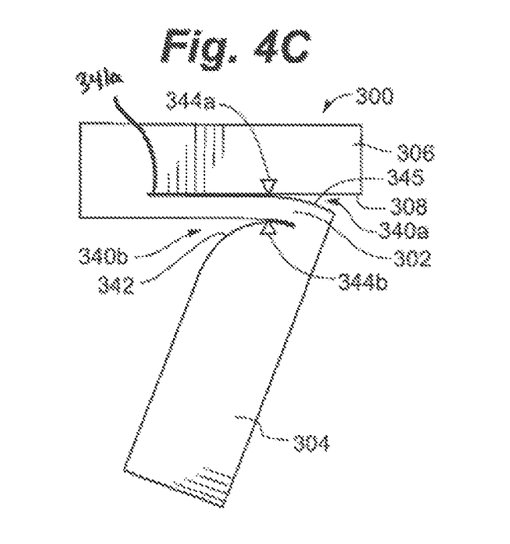
FIG. 4C is a partial side view of the flexible joint arrangement of FIG. 4A.

FIGS. 4A-4C depict a further embodiment of a flexure linkage 300. Wrapping surface 308 on base 306 is flat. Flexure member 302 begins curved around inner surface 342 of structural member 304 and flattens out, thereby widening kerf 340b and narrowing kerf 340a, as the device distracts. Fulcrum 344a, 344b again translates along flexure member 302 as the structural member 304 is expanded relative to base 306, providing increased expansion. As the structural member 304 is expanded relative to base 306, structural member 304 supports more of any load on linkage 300 in compression and less is supported by the flexure member 302 in tension. Points along the flexure member 302 to the left of the fulcrum 344a, 344b have a radius of curvature defined by the wrapping surface 308 while points to the right of the fulcrum 344a, 344b have a radius of curvature defined by the inner perimeter wrapping surface 342.

As depicted in the above figures, when the structural member is fully expanded relative to the base, the flexure member can at least partially rest against wrapping surface of base. Thus, any compressive load on structural member may be partially supported by base during transition or can completely rest on 345 with no load on flexure. Alternatively, a linkage can be configured such that no portion of the flexure rests on the base, so the entirety of any load on the linkage will be carried by the flexure.

The thickness of the flexure in relation to the bend radius of the wrapping surface determines the fatigue life of the flexure due to movement. In some embodiments, flexures can be configured and designed to have very long fatigue life. In one embodiment, a device made from nitinol having a thickness of the flexure members that is preferably between 8% and 10% of the bend radius of the wrapping surface, with a maximum thickness of 18% has an infinite fatigue life. In another embodiment, a flexure made from PEEK preferably has a thickness that is 4.5% to 6.4% of the bend radius, with a maximum thickness of 15%. In a further embodiment, a flexure comprised of annealed titanium can have a thickness of up to 18% of the bend radius. In other embodiments, flexures can be configured and designed to have a finite fatigue life associated with a predetermined range of maximum number of cycles of expansion and contraction.

Flexures can exhibit either plasticity, defined as permanent deformation, or elasticity, essentially infinite life. Flexures will exhibit plasticity if the ratio of the flexure thickness to the bend radius exceeds the percent elongation before yield of the material comprising the flexure. Flexures will exhibit elasticity if the ratio of the flexure thickness to the bend radius is less than the percent elongation before yield of the material. Where flexures operate elastically, they can be used in devices requiring repeated repositioning. If flexures are configured to operate plastically, they can support loading of increased magnitude indefinitely, but should be left at a predetermined position and not repositioned more than a limited number of times.

Figure 5:
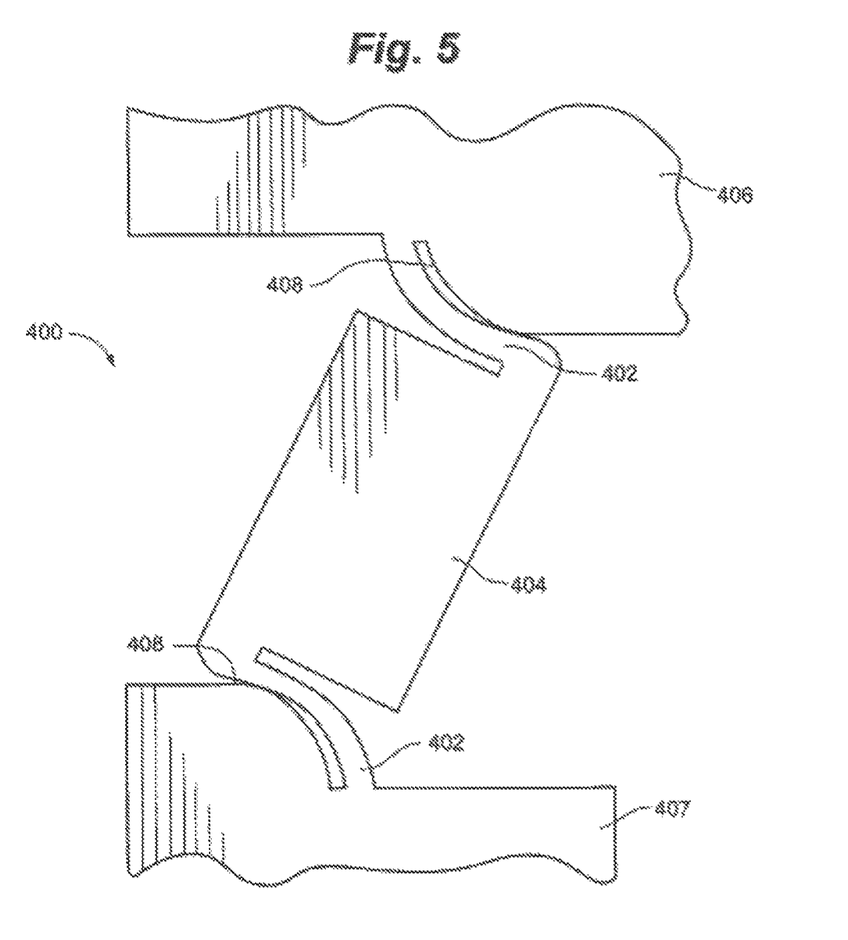
FIG. 5 is a partial side view of a flexible joint arrangement according to an embodiment of the present invention.
Figure 6A:
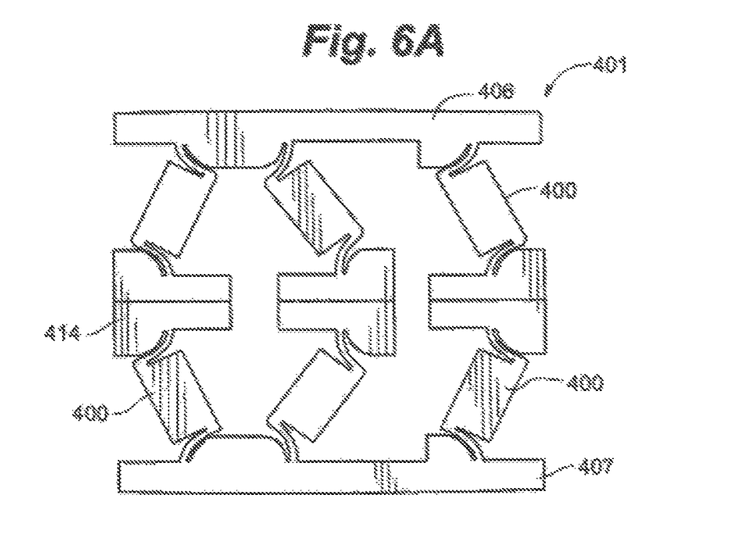
FIG. 6A is a side view of a device employing a plurality of flexible joint arrangements according to an embodiment of the present invention.
Figure 6B:
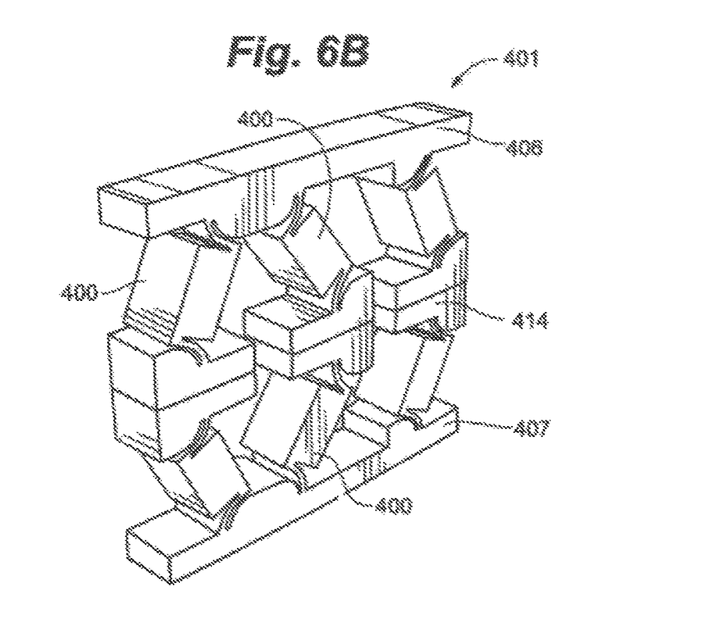
FIG. 6B is a perspective view of the device of FIG. 6A.
Figure 7A:
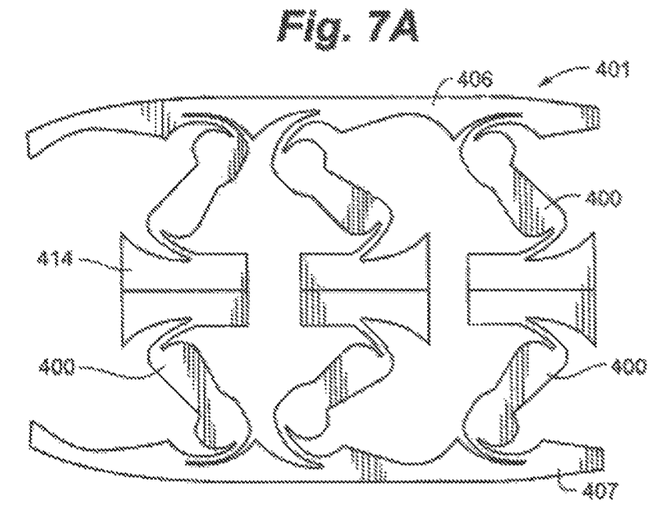
FIG. 7A is a side view of a device employing a plurality of flexible joint arrangements according to an embodiment of the present invention.
Figure 7B:
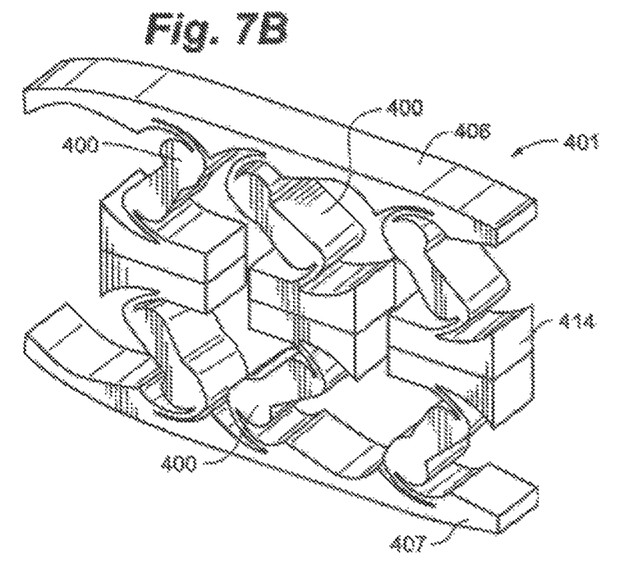
FIG. 7B is a perspective view of the device of FIG. 7A.

Referring to FIG. 5, a flexure linkage 400 according to an embodiment of the present invention can include a flexure member 402 positioned at each end of a structural member 404 connecting the structural member 404 to a top base 406 and a bottom base 407. This configuration essentially comprises a three bar linkage between the bases 406, 407, with the end bars (the flexure members 402) being flexible and the middle bar (the structural member 404) being rigid. Flexure linkage 400 can be used to distract top base 406 and bottom base 407 relative to each other. Flexure linkage 400 therefore includes two instantaneous axes of rotation that move along each flexure 402 as described above with reference to the fulcrum along which the flexure members bend as the linkage expands. The two axes of rotation are mirror images of each other and travel at different heights in the same plane that is transverse to the axes. Although flexure linkage 400 is depicted as having outwardly curved wrapping surfaces 408, such a flexure linkage 400 employing a flexure member 402 on each end could include wrapping surfaces of any other configuration. In some embodiments, wrapping surface 408 on top base 406 and wrapping surface 408 on bottom base 407 can have different geometries.

Figure 8A:
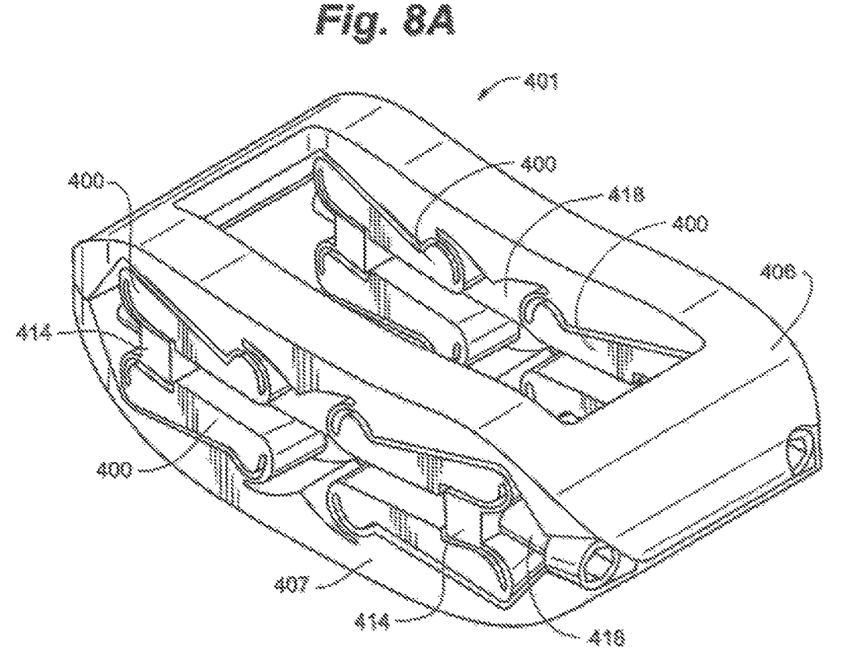
FIG. 8A is a perspective view of a device employing a plurality of flexible joint 5 arrangements according to an embodiment of the present invention.
Figure 8B:
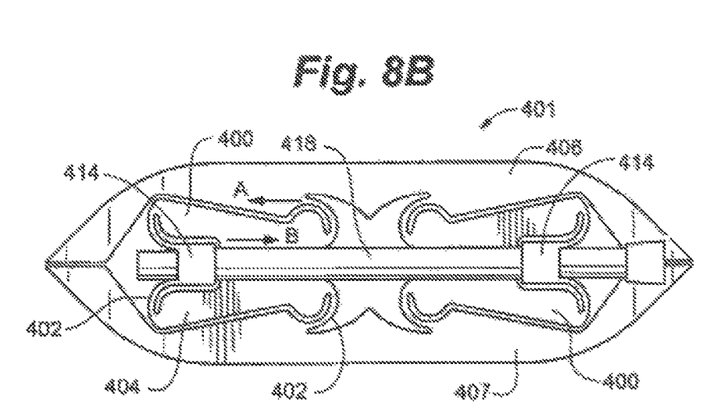
FIG. 8B is a side view of the device of FIG. 8A.

As can be seen in FIGS. 6A-6B and 7A-7B, a device 401 can include multiple flexure linkages 400. Flexure linkages 400 can be connected vertically between bases 406, 407 and/or aligned in a row lengthwise along bases 406, 407. Flexure linkages 400 can also situated side-by-side across a width of bases 406, 407 as shown in FIGS. 8A and 8B. Such devices 401 can include blocks 414 acting as common bases for vertically adjacent flexure linkages 400. Blocks 414 can be tapped to accommodate an expansion mechanism, such as a drive screw 418 (FIGS. 8A and 8B) that can be used to expand flexure linkages 400 and distract bases 406, 407.

Unlike many common scissor jacks, such as, for example, car jacks, device 401 can easily be distracted from its lowest, or most compressed, state. This is because the flexure members 402 on each end of a given structural member 404 are oriented such that the tensile loads on the flexure members 402 do not act towards each other, but instead pass by each other, like passing cars (see arrow A and arrow B in FIG. 8B). Common jacks, which do not utilize flexure members, may have difficulty distracting from the lowest state because the tensile loads can act "heads on" with each other, putting the device under strong internal horizontal compression but without a significant force component in the vertical direction at the lowest state that can easily initiate distraction. The tension in the flexure member required to support a compressive load is equal to the compressive load multiplied by the cosine of the angle of the rigid link divided by the sine of the rigid link. Because the sine of zero degrees, the angular position of normal scissor jacks in the compressed state, is equal to zero, the force required for initial distraction can be effectively very large. The rigid links of the device of various embodiments of the present invention may start off in the position of zero angular position, but because the flexure members are on opposing sides of the rigid links the effective angular position is non-zero, making the force required for initial distraction finite and generally smaller than a conventional scissor jack.

Although flexure members have been described herein as being generally planar, flexure members can have various other shapes. For example, flexure members could have an arcuate configuration. Flexure members could also include lips or ridges projecting upwardly from one or more surfaces. Additionally, flexure members could be curved along their width, creating a singularity or bias that could cause them to have a position, or positions, in which they are inclined to reside throughout the normal range of motion.

In some embodiments, flexible joint arrangements and devices employing flexible joint arrangements according to embodiments of the present invention can comprise a one-piece unitary body. This provides great cost savings over devices that require multiple pieces to be separately manufactured and assembled. In one embodiment, the device can be manufactured using wire or sink edm. In another embodiment, the device can be manufactured using three-dimensional printing techniques or the like. In some embodiments, portions of the flexible joint arrangements and devices, such as the flexure members, blocks and backstops, for example, can be machined separately and welded or otherwise attached to the device.

Flexible joint arrangements as disclosed herein and devices utilizing flexible joint arrangements can be constructed in various sizes, including, macro, micro, and nano sized applications.

In one embodiment, flexures on a macro scale may be made of a different material or made with a different material treatment than the rest of the structure and then affixed in position with welding, adhesives, or mechanical fasteners. In some embodiments, the flexures may be configured in a nesting geometry. The material from which the flexures are made could be cold rolled to improve its fatigue properties and then installed in the device.

In another embodiment, flexures on a macro scale could be laminated beams with a core of a stiff material, a softer material, or no material. Such lamination and material variation through the flexure itself would lead to precise control over the strength and fatigue properties of the flexures and the device employing the flexures. Specifically, a laminated beam having a soft core or no core at all would allow the flexure to get thinner as it bent further around the support structure, maintaining the operation of the flexure in the elastic region of the material from which it is made.

In another embodiment, in a device on a macro scale the surfaces against which the flexures roll could be machined and affixed such that the effective kerf at the instantaneous centers of rotation is effectively zero in the unloaded state. This would be advantageous because it would minimize the local stresses with the flexure and the structure, resulting in a stronger device, capable of greater fatigue life.

Flexures on a macro scale could also be layered with the same or different materials such that if one layer were to crack, the crack would not propagate through to the next layer.

On a micro scale, flexures could be manufactured with a layering process that would allow for different levels of the flexure to be doped with different materials enhancing the strength or fatigue properties of the flexure at different levels. For example, if sintering were used, Ti 6Al 4V Standard could be used for the main body of the flexure, while Ti 6Al 4V ELI could be used to create surface features given that the standard form of titanium has improved smooth fatigue properties and the ELI form of titanium has improved notched fatigue properties.

On the nano scale, many similar doping or material manipulation properties would also be available. Additionally ion intercalation could be used to move the blocks closer together or farther apart, resulting in what could be a chemically actuated device, sensor, or valve.

In all scales, the flexure itself could be replicated, mirrored, multiplexed, rotated, extruded, or revolved to create further novel structures or flexures.

Various embodiments of systems, devices and methods have been described herein. These embodiments are given only by way of example and are not intended to limit the scope of the present invention. It should be appreciated, moreover, that the various features of the embodiments that have been described may be combined in various ways to produce numerous additional embodiments. Moreover, while various materials, dimensions, shapes, etc. have been described for use with disclosed embodiments, others besides those disclosed may be utilized without exceeding the scope of the invention.

The invention claimed is:

1. An expandable device, comprising:
a first base member and a second base member;
a plurality of flexure assemblies disposed between the first base member and the second base member, wherein each flexure assembly comprises:
a first structural member connected to the first base member with a first flexure member;
an intermediate block connected to the first structural member with a second flexure member; and
a second structural member connected to the intermediate block with a third flexure member and to the second base member with a fourth flexure member, wherein each structural member is rotatable with respect to the first base member and the second base member via the corresponding flexure members to move the first base member relative to the second base member such that the first base member and the second base member are movable between a compressed configuration and an expanded configuration relative to each other,
wherein a wrapping surface is defined, in each of the first base member adjacent the first flexure, member, the intermediate block adjacent the second flexure member, the intermediate block adjacent the third flexure member and the second base member adjacent the fourth flexure member, and
wherein each wrapping surface provides a guide for rotation of the corresponding flexure member that, defines a traveling, instantaneous axis of rotation about which the flexure member rotates that moves along a path defined by an interface of the wrapping surface and the corresponding flexure member as, the flexure member rotates, wherein each point along each flexure member has a radius of curvature that changes only in discrete quantum steps without reversing from either a positive radius of curvature or a negative radius of curvature to the other of a positive radius of curvature and a negative radius of curvature as the first base member and the second base member are moved from the compressed configuration to the expanded configuration, and wherein the plurality of flexure assemblies, first base member and second base member comprise a unitary one-piece monolithic body.

2. The expandable device of claim 1, wherein one or more of the wrapping surfaces has a concave cross-sectional shape.

3. The expandable device of claim 1, wherein one or more of the wrapping surfaces has a convex cross-sectional shape.

4. The expandable device of claim 1, wherein one or more of the wrapping surfaces has a flat cross-sectional shape.

5. The expandable device of claim 1, wherein each flexure rotates elastically.

6. The expandable device of claim 1, wherein each wrapping surface provides a guide for rotation of the corresponding flexure member by interfacing with the flexure member as the flexure member rotates such that a portion of the flexure member contacting the wrapping surface conforms to a shape of the wrapping surface.

7. The expandable device of claim 1, further comprising a drive mechanism extending through the intermediate block, the drive mechanism rotatable to cause the first base member and the second base member to move between the compressed configuration to the expanded configuration.

8. The expandable device of claim 7, wherein the intermediate block translates along the drive mechanism as the drive mechanism is rotated.

9. The expandable device of claim 7, wherein the drive mechanism is a screw.

10. An expandable device, comprising:
a first base member and a second base member;
a plurality of flexure assemblies disposed between the first base member and the second base member, wherein each flexure assembly comprises:
a first structural member connected to the first base member with a first flexure member;
an intermediate block connected to the first structural member with a second flexure member; and
a second structural member connected to the intermediate block with a third flexure member and to the second base member with a fourth flexure member, wherein each structural member is rotatable with respect to the first base member and the second base member via the corresponding flexure members to move the first base member relative to the second base member such that the first base member and the second base member are axially expandable between a compressed configuration and an expanded configuration relative to each other, wherein each flexure member defines a traveling instantaneous axis of rotation about which the corresponding flexure members rotate as the first base member and the second base member are moved relative to each other such that the axes of rotation of each flexure member travel at different heights within a plane define transverse to the axes without overlapping as the first base member and the second base member are axially expanded and contracted relative to each other, and wherein the plurality of flexure assemblies, first base member and second base member comprise a unitary one-piece monolithic body.

11. The expandable device of claim 10, wherein a wrapping surface is defined in each of the first base member adjacent the first flexure member, the intermediate block adjacent the second flexure member, the intermediate block adjacent the third flexure member and in the second base member adjacent the fourth flexure member, wherein each wrapping surface provides a guide for rotation of the corresponding flexure member and defines a radius of curvature of at least a portion of the corresponding flexure member as the first base member and the second base member are axially expanded and contracted relative to each other.

12. The expandable device of claim 7, wherein each wrapping surface provides a guide for rotation of the corresponding flexure member by interfacing with the flexure member as the flexure member rotates such that a portion of the flexure member contacting the wrapping surface conforms to a shape of the wrapping surface.

13. The expandable device of claim 11, wherein one or more of the wrapping surfaces has a concave cross-sectional shape.

14. The expandable device of claim 11, wherein one or more of the wrapping surfaces has a convex cross-sectional shape.

15. The expandable device of claim 11, wherein one or more of the wrapping surfaces has a flat cross-sectional shape.

16. The expandable device of claim 11, further comprising a drive mechanism extending through the intermediate block, the drive mechanism rotatable to cause the first base member and the second base member to axially move between the compressed configuration to the expanded configuration.

17. The expandable device of claim 16, wherein the intermediate block translates along the drive mechanism as the drive mechanism is rotated.

18. The expandable device of claim 16, wherein the drive mechanism is a screw.

19. The expandable device of claim 10, wherein each flexure member rotates elastically.

* * * * *

UNITED STATES PATENT AND TRADEMARK OFFICE
CERTIFICATE OF CORRECTION

PATENT NO. : 10,060,469 B2
APPLICATION NO. : 15/198557
DATED : August 28, 2018
INVENTOR(S) : Jimenez et al.

Page 1 of 1

It is certified that error appears in the above-identified patent and that said Letters Patent is hereby corrected as shown below:

Column 8, Line 56, after "flexure" please delete ",".

Column 8, Line 62, after "that" please delete ",".

Column 8, Line 63, after "traveling" please delete ",".

Column 8, Line 66, after "as" please delete ",".

Column 9, Line 20, after "flexure" please insert --member--.

Column 10, Line 26, please delete "7" and insert --11--.

Signed and Sealed this
Twenty-third Day of October, 2018

Andrei Iancu
*Director of the United States Patent and Trademark Office*